(12) United States Patent
Boit et al.

(10) Patent No.: US 11,439,168 B2
(45) Date of Patent: Sep. 13, 2022

(54) NON-CRYSTALLISABLE D-ALLULOSE SYRUPS

(71) Applicant: ROQUETTE FRERES, Lestrem (FR)

(72) Inventors: Baptiste Boit, La Gorgue (FR); Geoffrey Lacroix, Lille (FR)

(73) Assignee: ROQUETTE FRERES, Lestrem (FR)

( * ) Notice: Subject to any disclaimer, the term of this patent is extended or adjusted under 35 U.S.C. 154(b) by 664 days.

(21) Appl. No.: 16/471,717

(22) PCT Filed: Jan. 5, 2018

(86) PCT No.: PCT/FR2018/050028
§ 371 (c)(1),
(2) Date: Jun. 20, 2019

(87) PCT Pub. No.: WO2018/127670
PCT Pub. Date: Jul. 12, 2018

(65) Prior Publication Data
US 2019/0328014 A1     Oct. 31, 2019

(30) Foreign Application Priority Data

Jan. 5, 2017 (FR) ..................... 17 50106

(51) Int. Cl.
| | | |
|---|---|---|
| *A23L 27/00* | (2016.01) | |
| *A23L 27/30* | (2016.01) | |
| *A23L 27/60* | (2016.01) | |
| *A23L 29/30* | (2016.01) | |
| *A23L 23/00* | (2016.01) | |
| *A23L 21/10* | (2016.01) | |
| *A21D 13/41* | (2017.01) | |
| *A21D 13/28* | (2017.01) | |
| *A21D 2/18* | (2006.01) | |
| *A23G 3/32* | (2006.01) | |

(Continued)

(52) U.S. Cl.
CPC .............. *A23L 27/33* (2016.08); *A21D 2/181* (2013.01); *A21D 13/28* (2017.01); *A21D 13/41* (2017.01); *A23G 3/32* (2013.01); *A23G 9/34* (2013.01); *A23L 21/10* (2016.08); *A23L 23/00* (2016.08); *A23L 27/63* (2016.08); *A23L 29/30* (2016.08); *B01D 61/027* (2013.01); *B01D 61/04* (2013.01); *C07H 1/06* (2013.01); *B01D 2311/04* (2013.01); *B01D 2311/2626* (2013.01); *C07H 3/02* (2013.01)

(58) Field of Classification Search
None
See application file for complete search history.

(56) References Cited

FOREIGN PATENT DOCUMENTS

| | | |
|---|---|---|
| CN | 103 333 935 A | 10/2013 |
| CN | 104 447 888 A | 3/2015 |

(Continued)

OTHER PUBLICATIONS

Takeshita et al., "Mass Production of D-Psicose from D-Fructose by a Continuous Bioreactor System Using Immobilized D-Tagatose 3-Epimerase," Journal of Bioscience and Bioengineering, 2000, vol. 90, No. 4, pp. 453-455.

(Continued)

*Primary Examiner* — Stefanie J Cohen
(74) *Attorney, Agent, or Firm* — Oliff PLC

(57) ABSTRACT

A D-allulose syrup including, besides D-allulose, a D-allulose dimer mass content, expressed in terms of dry mass, greater than 1.5%. Also, a method for producing the syrup and the use thereof for producing food or pharmaceutical products.

9 Claims, 5 Drawing Sheets

(51) Int. Cl.
*A23G 9/34* (2006.01)
*B01D 61/02* (2006.01)
*B01D 61/04* (2006.01)
*C07H 1/06* (2006.01)
C07H 3/02 (2006.01)

(56) References Cited

FOREIGN PATENT DOCUMENTS

| | | |
|---|---|---|
| CN | 103 059 071 B | 3/2016 |
| FR | 3 016 628 A1 | 7/2015 |
| JP | 2001-354690 A | 12/2001 |
| WO | 2011/119004 A2 | 9/2011 |
| WO | 2015/032761 A1 | 3/2015 |
| WO | 2015/094342 A1 | 6/2015 |
| WO | 2016/064087 A1 | 4/2016 |
| WO | 2016/135458 A1 | 9/2016 |

OTHER PUBLICATIONS

Salehi, Fakhreddin, "Current and future applications for nanofiltration technology in the food processing," Food and Bioproducts Processing, 2014, vol. 92, pp. 161-177.

Mar. 7, 2018 International Search Report issued in International Patent Application No. PCT/FR2018/050028.

NON-CRYSTALLISABLE D-ALLULOSE SYRUPS

FIELD OF THE INVENTION

The invention relates to a D-allulose syrup, one of the advantageous properties of which is that it is less crystallizable than the prior art syrups. Another subject of the invention relates to the use of this D-allulose syrup for producing food products or pharmaceutical products. Another subject of the invention relates to a process for producing this D-allulose syrup.

PRIOR ART

D-allulose (or D-psicose) is a rare sugar which has a sweetening power equal to 70% of that of sucrose. Contrary to the latter, D-allulose does not cause weight gain since it is not metabolized by human beings. It has a very low calorie content (0.2 kcal per gram) and it thus prevents an increase in body fat. Furthermore, studies have shown that D-allulose is non-cariogenic, or even anti-cariogenic. Thus, these properties have recently generated a very great deal of interest from the food and pharmaceutical industries.

D-allulose is generally obtained enzymatically, by reacting an aqueous solution of D-fructose with a D-psicose epimerase as described for example in application WO2015/032761 A1 in the name of the applicant. Whatever the enzyme used, the reaction is not total and the amount of fructose converted into D-allulose after epimerization is less than 30%.

Thus, starting from the composition resulting from the epimerization reaction, it is necessary to carry out a step of separating the D-allulose, in order to isolate it from the other constituents present and in particular from the fructose. In order to carry out this separation, chromatography of the composition resulting from the epimerization reaction is very generally carried out, for example by continuous chromatography of simulated mobile bed type, thereby making it possible to isolate a fraction rich in D-allulose.

Document JP 2001354690 A describes a process for purifying a D-allulose composition starting from a mixture of fructose and D-allulose, said process comprising a separation step consisting of a step of continuous chromatography using a particular sequence of sampling of the various products of the mixture. A fraction rich in D-allulose (the D-allulose richness of which can reach 98%) and a fraction rich in fructose are recovered. The recovery yield in the fraction rich in D-allulose is 96%.

At the end of the abovementioned separation steps, liquid compositions rich in D-allulose are obtained. Thus, these liquid compositions, generally called syrups, are used for the production of food or pharmaceutical products. By way of example, application WO 2015/094342 in the name of the applicant describes the production of solid food products comprising a D-allulose syrup, comprising from 50% to 98% of D-allulose and a native protein. It is mainly in this syrup form that various companies have to date announced the marketing of D-allulose.

Document WO 2016/135458 describes, for its part, syrups comprising, relative to its dry mass, at least 80% of allulose, and studies their stability over time. No protocol for producing this syrup is described. The composition of the syrups is analyzed by high-performance liquid chromatography, which is presented as the standard method for analyzing syrups of this type. The syrups described in said application are presented as being crystallizable at low temperature.

However, for some applications, there may be an advantage in having a D-allulose syrup which is non-crystallizable or even less crystallizable, this being even at low temperature. This is in particular the case when the D-allulose must be used as a humectant, since a compound exhibits this humectant function only when it is in the form of a solute, and thus non-crystallized. Other applications also require the sugar not to crystallize in the final product in order to obtain the desired properties. For example, in order to obtain a smooth texture, it is necessary for there to be no crystallization of the D-allulose in sauces, starch jellies, soft caramels, jams or fruit fillings. Likewise, it is preferable for there to be no crystalline deposit in liquid solutions such as vinaigrettes or drinks. Foods in the form of bars (nutritional bars, cereal bars, fruit and nut bars, etc.) are, for their part, softer if the sugar does not crystallize in the final product.

It has also been observed that syrups can exhibit storage instability by forming crystals in suspension over time, in particular when this storage is done at low temperature. In this case, and in particular when these crystals grow, the viscosity of the syrup can drastically increase and it can become necessary to reheat the syrup until the crystals in suspension are melted in order to be able to easily handle it again. It may thus be of interest to provide novel syrups which exhibit improved storage stability and which crystallize little or not at all, even at low temperature.

By carrying out a great deal of research, the applicant has been able to note that, in a process for producing D-allulose syrups, particular impurities form during the process. Said impurities have, to the applicant's best knowledge, never been reported in the literature. It has been possible for the applicant to identify them, by using a particular gas chromatography technique, as being D-allulose dimers. The applicant has also been able to show that these dimers, contrary to other impurities such as glucose or fructose, have a very significant anti-crystallizing effect. These D-allulose dimers form during the process and their presence in the D-allulose syrup is systematic.

Going beyond this observation, the applicant has also continued its efforts in order to provide, for a given dry matter content and a given D-allulose content, novel syrups which exhibit a less crystallizable nature than those of the prior art. To do this, it has developed a process which allows it to provide syrups which have an increased content of D-allulose dimers. This makes the syrup less crystallizable, thereby making it possible to facilitate the storage thereof for the purpose of subsequent use, in particular at low-temperature.

SUMMARY OF THE INVENTION

The subject of the invention is thus a D-allulose syrup comprising, in addition to the D-allulose, a mass content of D-allulose dimer, determined by gas chromatography (GC), greater than 1.5%.

This syrup has the advantage of being less crystallizable than the prior art syrups, or even non-crystallizable under certain temperature conditions, thereby allowing it to be more stable with respect to storage. This syrup can also be advantageously used in the abovementioned applications.

Another subject of the invention relates to a process for producing the syrup of the invention. This process comprises:

a step of providing a D-allulose composition comprising D-allulose dimers;
a step of nanofiltration of said D-allulose composition;
a step of recovering the nanofiltration retentate;
a step of concentrating this retentate so as to provide the D-allulose syrup.

The use of a nanofiltration step makes it possible to recover a retentate enriched with D-allulose dimer and to thus obtain, after concentration, the syrup of the invention.

As mentioned above, the applicant has been able to note that, systematically, during the production of D-allulose syrups, particular impurities form during the process. Said impurities have, to the applicant's best knowledge, never been reported in the literature. This is explained by the fact that, with the high performance liquid chromatography technique conventionally used to measure the purity of D-allulose, these impurities are not detected on the chromatograms (see FIGS. 4 and 5). It is by using a gas chromatography technique that the applicant has been able to detect the presence thereof (see FIGS. 6 and 7).

With regard to document WO 2015/094342, this document uses syrups comprising D-allulose. However, no method for preparing this syrup is indicated. In point of fact, as emerges in the remainder of the description, the choice of the conditions of the preparation and in particular the concentration steps has an essential impact on the amount of D-allulose dimers formed, which have up until now never been reported. The document thus does not describe the syrup of the invention. The same is document WO 2016/135458 true of already mentioned or else document WO 2015/032761 which does not even exemplify such a syrup.

With regard to document JP2001354690 A mentioned above, it describes the separation of fructose and allulose, by chromatography, from a composition comprising these two consitutents. However, it does not describe the preparation of a D-allulose syrup. In point of fact, since the choice of the conditions of the steps preparing this syrup and in particular concentrating the latter have an essential impact on the amount of D-allulose dimers, this document does not therefore describe the syrup of the invention.

Documents WO 2011/119004 A2, WO 2016/064087, CN 104447888 A and CN 103333935 A describe the production of crystalline compositions comprising D-allulose, but do not describe the production of D-allulose syrups.

The invention also relates to a D-allulose syrup that can be obtained by means of the process of the invention.

BRIEF DESCRIPTION OF THE FIGURES

FIG. 1 represents the circuit for production of a non-crystallizable allulose syrup.

FIG. 2 represents a circuit for production of a non-crystallizable allulose syrup with recycling loops.

FIG. 3 represents the curve of permeation relative to the nanofiltration step, that is to say the flow as a function of the volume concentration factor.

FIG. 4 represents an HPLC chromatogram of a composition rich in D-allulose sampled in the process of the invention, before nanofiltration.

FIG. 5 represents an HPLC chromatogram of a retentate sampled in the process of the invention, that is to say after nanofiltration.

FIG. 6 represents a GC chromatogram, in the zone characteristic of the dimers, of a composition rich in D-allulose sampled in the process of the invention, before nanofiltration.

FIG. 7 represents a GC chromatogram, in the zone characteristic of the dimers, of a retentate sampled in the process of the invention, that is to say after nanofiltration.

FIG. 8 represents the dry matter of the supernatant after 1 month of storage at 4 and 15° C. as a function of the D-allulose dimer content.

DETAILED DESCRIPTION OF THE INVENTION

Figure 1:
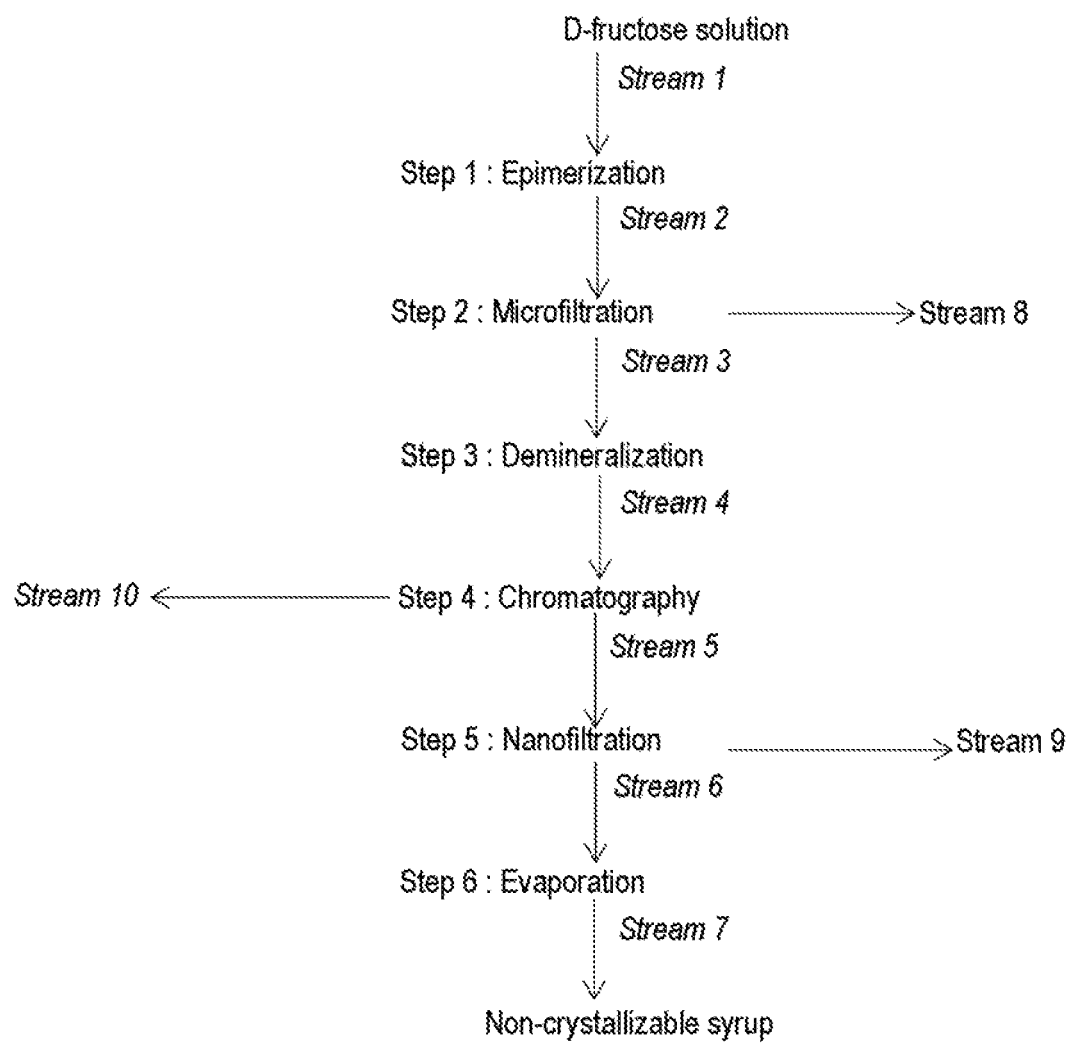
FIG. 1.

The D-allulose syrup of the invention is an aqueous solution which is poor in D-allulose dimers. The term "aqueous composition" or "aqueous solution" is generally intended to mean a composition or a solution of which the solvent consists essentially of water. The term "D-allulose dimer" is intended to mean a compound comprising a D-allulose condensed with at least a second identical or different monosaccharide. These dimers are for example dimers of D-allulose-D-allulose type.

As previously described, the fact that the amount of D-allulose dimers included in the syrup is enriched, i.e. that its mass content expressed as dry mass is, according to the invention, greater than 1.5%, has made it possible to obtain a less crystallizable syrup.

These dimers could be detected by GC and could not be detected during the HPLC analysis, as demonstrated in FIGS. 4 to 7. It follows from this that the mass amounts of the various constituents, expressed as dry mass, are in the present application systematically determined by GC. In order to determine the amounts of each of the species in the composition, the sample generally undergoes a treatment step in order to convert the various species present into methoximated trimethylsilyl derivatives. The mass amounts of each of the species are expressed in the present application, unless otherwise mentioned, relative to the total dry mass.

The amounts of glucose, of fructose and of allulose can be determined in a gas chromatograph equipped with an injector heated to 300° C., equipped with a flame ionization detector (FID) heated to 300° C. and equipped with a 40-meter DB1 capillary column, having an internal diameter of 0.18 mm and a film thickness of 0.4 μm, the column temperature being programmed in the following way: from 200° C. up to 260° C. at a rate of 3° C./min, then from 260° C. up to 300° C. at 15° C./min, hold at 300° C. for 5 min.

The term "amount of D-allulose dimers" is intended to mean the difference between the total amount of dimers in a sample, determined by GC, and the amount of the known dimers possibly present, which are glucose-glucose dimers such as maltose and isomaltose. The amount of these glucose-glucose dimers can be very small, or even non-existent. In the syrup of the invention, the mass amount of glucose-glucose dimers is generally less than 2%, often less than 1%, or even less than 0.2% or less than 0.1%.

The possible amount of glucose-glucose dimers can be determined under the same conditions as those previously described for glucose, fructose and D-allulose:
  by carrying out a hydrolysis of the glucose-glucose dimers of the sample;
  by determining the amount of total glucose in the same chromatogram and under the same conditions, said total glucose comprising the initial glucose termed free and the glucose resulting from the hydrolysis of the glucose-glucose dimers;
  by subtracting, from this amount of total glucose, the amount of initial glucose of the sample.

The total amount of dimers can, for its part, be determined in a gas chromatograph under the same conditions as previously described, with the difference that the column used is a 30-meter DB1 capillary column, having an internal diameter of 0.32 mm and a film thickness of 0.25 μm, and the column temperature is programmed in the following way: from 200° C. up to 280° C. at a rate of 5° C./min, hold at 280° C. for 6 min, then from 280° C. up to 320° C. at 5° C./min, hold at 320° C. for 5 min.

The method is described in greater detail in the Examples section.

The D-allulose syrup comprises, in addition to the D-allulose, a mass content of D-allulose dimer, determined by gas chromatography (GC), greater than 1.5%.

It may be greater than 1.8% and in particular range from 1.9% to 20%, preferably from 2.0% to 15%, for example from 2.1% to 8%, or even from 2.4% to 5%.

According to one variant, the syrup of the invention comprises D-fructose and D-allulose in a D-fructose/D-allulose mass ratio of between 50/50 and 40/60 and essentially consists of D-fructose, D-allulose and D-allulose dimers. This syrup has the advantage of having the same sweetening power as sucrose.

According to another preferred variant, the syrup of the invention comprises a D-allulose content, expressed as dry mass, greater than or equal to 75%. The syrup of the invention has the advantage of being able to exhibit a nature that is not very crystallizable, even when it reaches this D-allulose content. This is particularly surprising since it is known that the more of a compound (in this case D-allulose) a syrup predominantly comprises, the greater the tendency for this syrup to exhibit a crystallizable nature. According to the invention, the presence of the D-allulose dimers starting from more than 1.5% by mass, expressed as dry mass, in the syrup, makes it possible to render it particularly less crystallizable.

The syrup of the invention can have a D-allulose content, expressed as dry mass, greater than or equal to 80%, for example greater than or equal to 85%, in particular greater than or equal to 90%.

The D-allulose syrup can advantageously comprise, relative to its dry mass:
  from 75% to 99% of D-allulose;
  from 0% to 20% of D-fructose;
  from 0% to 10% of glucose;
  from 1.5% (limit excluded) to 20% of D-allulose dimer, in particular from 1.9% to 20%, preferably from 2.0% to 15%, for example from 2.1% to 8%, or even from 2.4% to 5%.

The D-allulose syrup can have a dry matter content greater than 50%, for example ranging from 65% to 85%, in particular ranging from 70% to 83%, for example from 75% to 82%. The higher the dry matter content, the more easily crystallizable the syrup. However, when the dry matter content is high, the viscosity of the syrup can increase, which can result in difficulties in handling it.

A D-allulose syrup is conventionally obtained by means of a process comprising:
  a step of providing an aqueous composition comprising D-allulose;
  a step of concentrating said aqueous composition so as to form the D-allulose syrup.

The syrup of the invention can be prepared according to a process described in detail below which comprises, prior to the concentrating step, a nanofiltration step.

This nanofiltration step makes it possible to increase the amount of D-allulose dimers in the syrup of the invention. This nanofiltration step takes place before the step of concentrating the composition rich in D-allulose. This step thus allows the provision of a D-allulose syrup of which the D-allulose dimer content is richer than that obtained from one and the same process not using this nanofiltration step.

In the nanofiltration step, which is essential to the process of the invention, two fractions are formed when a composition of D-allulose is subjected to nanofiltration:
  a permeate, which is poor in D-allulose dimers;
  and also a retentate, which is enriched with D-allulose dimers.

In FIG. 1, which represents a circuit for producing syrup of the invention, the Stream 6 represents the retentate and the Stream 9 represents the permeate. For illustrative but non-limiting reasons, unless otherwise indicated, the Streams indicated in the remainder of the description refer to the streams of the production circuit of this FIG. 1.

The terms "poor in D-allulose dimers" and "enriched with D-allulose dimers" are obviously relative to the content of D-allulose oligomers of the composition to be nanofiltered.

The nanofiltration retentate is an intermediate which allows the production of the D-allulose syrup of the invention.

A subject of the invention thus relates to a process for producing syrup, which comprises:
  a step of providing an aqueous D-allulose composition comprising D-allulose dimers;
  a step of nanofiltration of said D-allulose composition so as to provide a retentate and a permeate;
  a step of recovering the nanofiltration retentate;
  a step of concentrating this retentate so as to provide the D-allulose syrup of the invention.

In order to carry out the nanofiltration step of use in the invention, the composition to be nanofiltered is passed through a nanofiltration membrane. It generally has a dry matter content ranging from 5% to 15%.

The temperature of this composition to be nanofiltered can range from 10 to 80° C., generally from 15 to 50° C., often around 20° C.

Those skilled in the art will know how to choose the membrane of use in this separation. This nanofiltration membrane can have a cut-off threshold of less than 300 Da, preferably ranging from 150 to 250 Da. Ideally, the membrane has an $MgSO_4$ rejection rate of at least 98%. It may in particular be a membrane of Dairy DK or Duracon NF1 type manufactured by GE®.

The pressure applied to the membrane can also vary widely and can range from 1 to 50 bar, preferably from 5 to 40 bar, most preferentially from 15 to 35 bar.

This nanofiltration step can be accompanied by a diafiltration phase.

Preferably, the volume concentration factor (FCV) of the nanofiltration ranges from 2 to 20. This volume concentration factor is easily regulated by those skilled in the art.

This nanofiltration step can be carried out continuously.

At the end of this nanofiltration step, the retentate recovered can comprise, relative to its dry mass, from 0.8% to 20% of D-allulose dimers, for example from 1.5% to 15%, in particular from 2% to 5%. It can for example comprise, by dry mass:
  from 75% to 99% of D-allulose;
  from 0% to 20% of D-fructose;
  from 0% to 10% of glucose;
  from 0.8% to 20% of D-allulose dimers, for example from 1.5% to 15%, in particular from 2% to 5%.

It goes without saying that the process according to the invention can comprise other steps, such as the other steps which appear in the conventional process previously described and which will subsequently be described in detail. The process according to the invention can also comprise additional purification steps and also intermediate diluting or concentrating steps with a view to regulating the dry matter content and thus to carrying out the various steps of the process of the invention under the best conditions. All of these steps can be carried out continuously.

The syrup of the invention generally has a dry matter content greater than or equal to 50%. To increase the dry matter content (the retentate has a dry matter content lower than 50%), it is necessary to carry out a concentrating step, during which the D-allulose dimer content can increase. The formation of D-allulose dimers can also occur during this concentrating step, in particular when the temperature is high. It is thus possible to select conditions which make it further possible to increase the amounts formed of these dimers. The concentrating step can be carried out under vacuum or at ambient temperature under vacuum. A step under vacuum makes it possible to decrease the temperature required for the evaporation and to reduce the duration of this concentrating step. It can be carried out at a temperature ranging from 30 to 100° C. This concentrating step can be carried out in a single-stage evaporator, a multi-stage evaporator, for example a double-stage evaporator. At the end of the concentrating step, the D-allulose syrup of the invention can be obtained. It comprises a D-allulose dimer content greater than 1.5%. Generally, the mass content of D-allulose dimers in the syrup of the invention is greater than 1.8% and can in particular range from 1.9% to 20%, preferably from 2.0% to 15%, for example from 2.1% to 8%, or even from 2.4% to 5%.

The process of the invention also comprises a step of providing an aqueous D-allulose composition comprising D-allulose dimers. The mass contents of the various constituents of the syrup (and in particular the possible D-allulose, D-fructose and glucose) are principally determined by the contents of each of these constituents included in the aqueous D-allulose composition provided. For example, if the aqueous D-allulose composition provided has a high D-allulose content, the permeate and the syrup obtained from this permeate also have a high D-allulose content.

A conventional process for producing a D-allulose composition comprising D-allulose dimers comprises:
a step of providing a D-fructose solution;
a step of epimerizing said solution so as to form a D-allulose composition comprising D-fructose and D-allulose;
optionally, a chromatography step so as to enrich the D-allulose composition with D-allulose;
a step of concentrating the optionally enriched D-allulose composition.

Thus, according to the process of the invention, for providing the D-allulose composition, a step of chromatography of a composition comprising D-allulose and D-fructose can be carried out. In this case, this composition comprising D-allulose and D-fructose is advantageously obtained by epimerization of a D-fructose solution.

The D-allulose composition obtained after the chromatography step, which has a D-allulose content greater than that of the composition obtained at the end of the epimerizing step, comprises D-allulose dimers. In addition to this D-allulose composition, a composition rich in D-fructose or "raffinate" is also formed during this chromatography step.

The composition of D-fructose provided (Stream 1) for carrying out the epimerizing step can be a D-fructose syrup, which can be obtained by dissolving D-fructose crystals in water or a glucose/D-fructose syrup. Preferentially, this composition comprises a glucose/D-fructose syrup which comprises at least 90% by dry weight of D-fructose, preferentially at least 94% of D-fructose.

Figure 2:
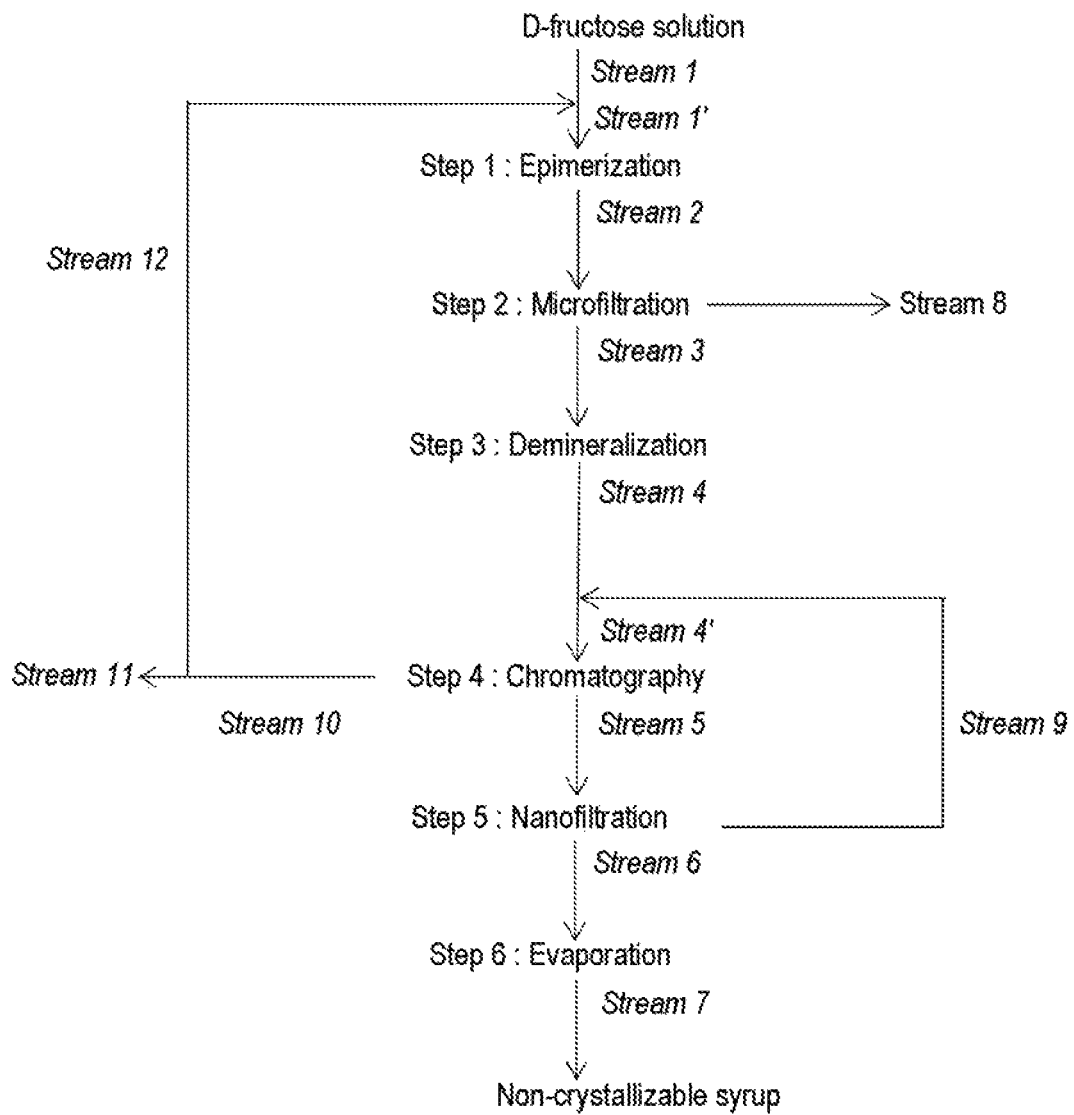
FIG. 2.

In one mode represented in FIG. 2, the D-fructose composition provided for carrying out the subsequent epimerizing step is a mixture (Stream 1') of this D-fructose syrup with at least one recycled fraction which may be the raffinate (all of the raffinate or a part) (Stream 10 or 12), it being possible for this recycled fraction to comprise a greater amount of D-allulose.

The D-fructose composition subjected to the epimerizing step can comprise:
from 0% to 10% of D-allulose;
from 70% to 100% of D-fructose;
from 0% to 10% of glucose;
from 0% to 15% of D-allulose dimer.

The epimerizing step is carried out using the D-fructose composition previously provided, optionally after regulation of the dry matter content. This step is generally carried out at a dry matter content ranging from 30% to 60%, often from 45% to 55%. An enzyme of D-psicose epimerase type or a composition comprising this enzyme is introduced into this composition. The composition comprising this enzyme may be a lyophilisate of a host microorganism which synthesizes D-psicose epimerase, said microorganism possibly being *Bacillus subtilis*, in particular the one described in application WO2015/032761 A1. The pH is regulated according to the enzyme used, for example at a pH ranging from 5.5 to 8.5. The reaction can be carried out by heating at a temperature ranging from 40 to 70° C., often from 45 to 60° C. The reaction can last from 0.1 to 100 hours, for example from 0.2 to 60 hours. This reaction can for example be carried out on an enzymatic column, thereby having the advantage of also working continuously on this step. It is also possible, in order to operate continuously, to work sequentially with several reactors. In order to carry out this epimerizing step, use may particularly be made of the teaching of document WO 2015/032761 A1.

At the end of the reaction, a composition comprising D-fructose and D-allulose, generally according to a D-fructose/D-allulose weight ratio ranging from 85/15 to 55/45, often according to a D-fructose/D-allulose weight ratio ranging from 80/20 to 60/40, is formed. This ratio depends on the epimerization parameters used and, quite obviously, on the amount of D-allulose and of D-fructose in the D-fructose composition provided in the epimerizing step; the amount of D-allulose in this composition may in particular be greater in the case of recycling.

At the end of this epimerizing step, if necessary, a filtration step can be carried out in order to recover the cell debris possibly present, in particular when a lyophilisate of a host microorganism is used. This step may consist of a microfiltration step. The microfiltered composition corresponds to Stream 3 and the cell debris is recovered in Stream 8.

Figure 3:
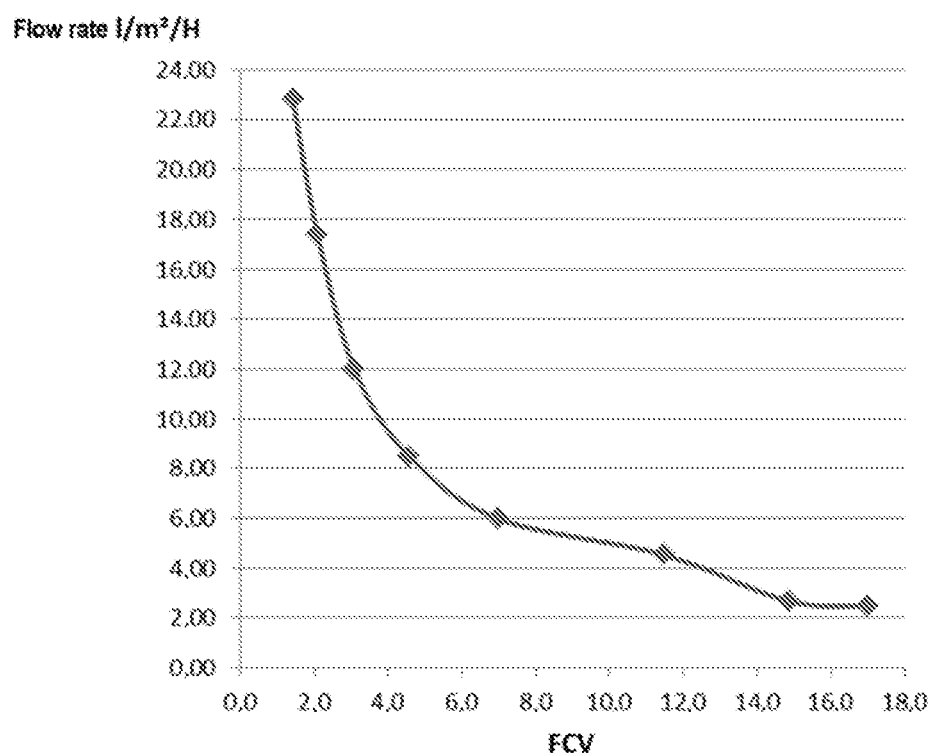
FIG. 3.
Figure 4:
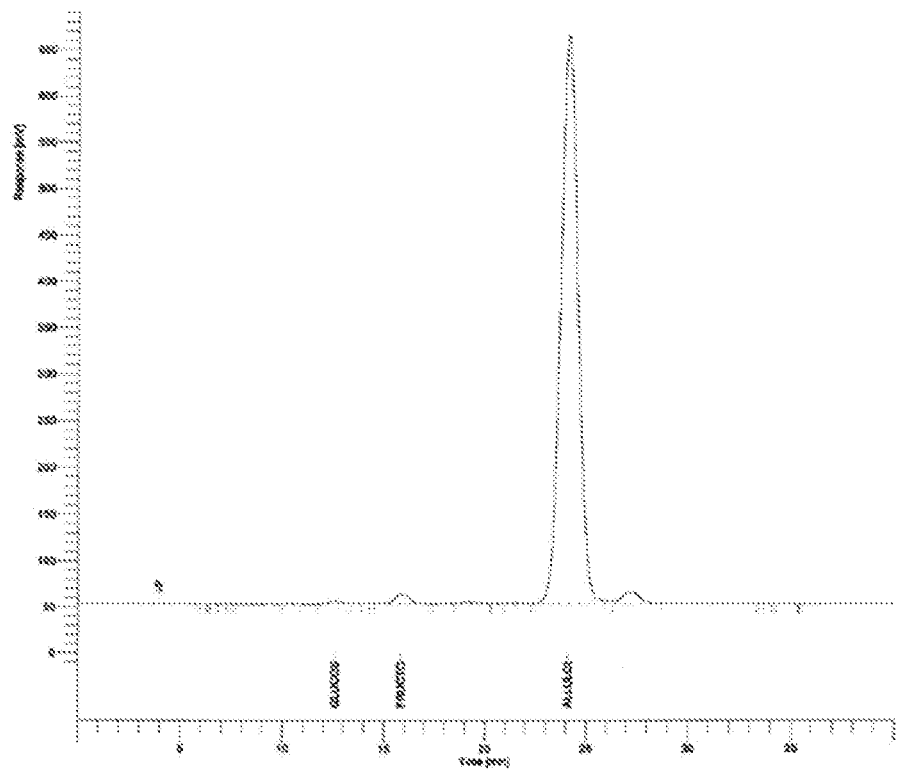
FIG. 4.
Figure 5:
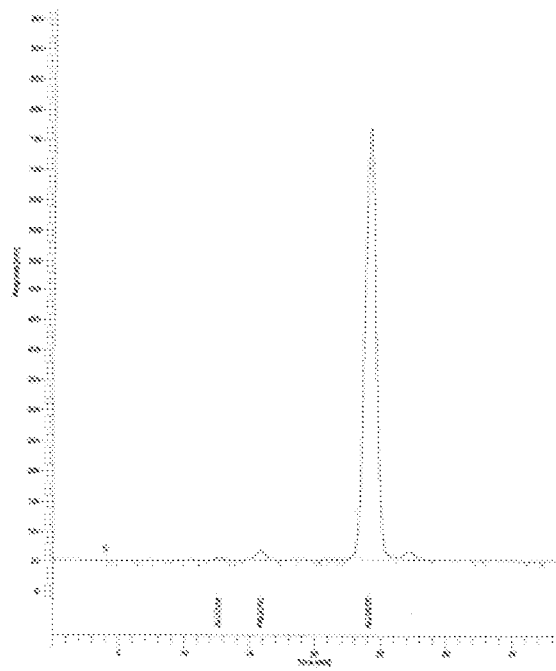
FIG. 5.

In the process of the invention, additional purifying steps can also be carried out. Generally carried out, before the chromatography step, is a step of demineralizing the composition comprising D-fructose and D-allulose (Stream 3), which can be carried out by passing it through one or more cationic ion exchange resins (for example a cationic resin of Dowex 88 type), anionic ion exchange resins (for example an anionic resin of Dowex 66 type) and a cationic-anionic mixture. In FIG. 3, this composition corresponds to Stream 4. The composition comprising D-fructose and D-allulose obtained is then demineralized and generally has a resistivity greater than 100 kΩ·cm$^{-1}$. It is also possible to carry out, before this demineralizing step, a step of decoloring the composition comprising D-fructose and D-allulose, for example by passing it over a column comprising active carbon.

The composition subject to the chromatography step can comprise, relative to its dry mass:
- from 22% to 45% of D-allulose, generally from 23% to 37%;
- from 45% to 75% of D-fructose, generally from 46% to 70%;
- from 0% to 10% of glucose;
- from 2% to 10% of D-allulose dimer.

In order to carry out this chromatography step, it is possible to use any type of continuous chromatography, in particular of Simulated Moving Bed (SMB) type, of Improved Simulated Moving Bed (ISMB) type, of Divide Improved Simulated Moving Bed (DISMB) type, of Sequential Simulated Moving Bed (SSMB) type or of Nippon Mitsubishi Chromatography Improved (NMCI) type. Water is generally used as eluent. The chromatograph can be equipped with several columns in series, for example from 4 to 8 columns. The columns comprise ion exchange resin, for example a cationic resin for exchanging calcium ions. The dry matter content of the composition comprising D-fructose and D-allulose can range from 40% to 70%, and is generally approximately 50%. The temperature of the composition during the chromatography generally ranges from 40 to 80° C., preferably from 55 to 65° C. This chromatography lasts for the amount of time required to obtain satisfactory separation and can last for several hours.

At the end of this step, a composition rich in D-allulose (Stream 5) which can comprise, relative to its dry matter content, at least 80% of D-allulose, advantageously at least 90% of D-allulose, is obtained. This composition rich in D-allulose can have a dry matter content ranging from 5% to 15%. At the end of this step, a raffinate (Stream 10), which generally comprises, relative to its dry matter content, at least 75% of D-fructose, often at least 80% of D-fructose, is also obtained. This raffinate generally has a dry matter content ranging from 15% to 30% approximately.

The process according to the invention can comprise a step of recycling at least one part of the nanofiltration permeate (Stream 9 of FIG. 2) and/or of the raffinate (Stream 10 of FIG. 2).

The syrup can be used for the production of food products or pharmaceutical products. The syrups of the invention can thus be used in the known applications of D-allulose and, generally, sweeteners. The syrup of the invention is advantageously used in applications where it is preferable for there to be no crystallization. Thus, the syrup of the invention is advantageously used for the production of drinks, caramels, starch jelly, sauces, vinaigrettes, jams, fruit filling, nutritional bars, cereal bars, pizzas, fruit and nut bars, milk products such as yoghurts or ice creams, or sorbets or as a humectant.

The invention will now be illustrated in the Examples section below. It is pointed out that these Examples do not limit the present invention.

EXAMPLES

Analytical Methods
Gas Chromatography
The gas chromatograph used is of Varian 3800 type and is equipped with:
- A split-splitless injector (with or without dividers);
- A flame ionization detector (FID);
- A computer system for processing the signal from the detector;
- An automatic sampler (type 8400).

The various amounts are determined by gas chromatography in the form of methoximated trimethylsilyl derivatives, then quantified by the internal calibration method.

Determination of the D-Allulose, D-Fructose and Glucose Contents

The response coefficients applied are 1.25 for D-allulose and D-fructose and 1.23 for glucose. The other monosaccharides are not detected.

Preparation of the Sample

In a dish for taring, weigh out 100 to 300 mg of the sample to be tested+10 ml of internal standard solution consisting of methyl α-D-glucopyranoside at 0.3 mg/ml in pyridine. Remove 0.5 ml from the dish for taring and place in a 2 ml pot and evaporate to dryness under a nitrogen stream. Add 20 mg of methoxylamine hydrochloride and 1 ml of pyridine. Stopper and leave in the Reacti-Therm® incubation system at 70° C. for 40 min. Add 0.5 ml of N,O-Bis (trimethylsilyl)trifluoroacetamide (BSTFA). Heat for 30 min at 70° C.

Chromatographic Conditions

Column: DB1 capillary 40 meters, internal diameter of 0.18 mm, film thickness 0.4 μm, 100% constituted of dimethylpolysiloxane, non-polar (J&W Scientific ref.: 121-1043)

Column temperature: 100° C. programming up to 260° C. at a rate of 3° C./min, then up to 300° C. at 15° C./min, maintain for 5 min at 300° C.

Injector temperature: 300° C.
Detector temperature: 300° C. (Range 10$^{-12}$)
Pressure: 40 psi (constant flow rate)
Vector gas: Helium
Injection mode: Split (Split flow rate: 100 ml/min)
Injected volume: 1.0 μl D-allulose, D-fructose and glucose were detected in this order. D-allulose, which was unknown, has a retention time under these conditions of between 39.5 and 40 minutes.

Determination of the contents of D-allulose dimers and glucose-glucose dimers

The response coefficients applied are 1.15 for the D-allulose dimers and maltose, and 1.08 for isomaltose. The other glucose dimers were not detected.

Preparation of the Sample:

In a dish for taring, weigh out 100 to 300 mg of the sample to be tested+10 ml of internal standard solution consisting of Phenyl beta-D-glucopyranoside at 0.3 mg/ml in pyridine. Remove 0.5 ml from the dish for taring and place in a 2 ml pot and evaporate to dryness under a nitrogen stream.

Take up with 0.5 ml of the solution of hydroxylamine hydrochloride at 40 g/l in pyridine, stopper, stir and leave at 70° C. for 40 min.

Add 0.4 ml of BSTFA and 0.1 ml of N-Trimethylsilylimidazole (TSIM). Heat for 30 min at 70° C.

Chromatographic Conditions

Column: DB1 capillary 30 meters, internal diameter of 0.32 mm, film thickness 0.25 μm (J&W Scientific ref.: 123-1032)

Column temperature: 200° C. programming up to 280° C. at a rate of 5° C./min (maintain for 6 min), then up to 320° C. at 5° C./min, maintain for 5 min at 320° C.

Injector temperature: 300° C.

Detector temperature: 300° C. (Range $10^{-12}$) Pressure: 14 psi (constant flow rate)

Vector gas: Helium

Injection mode: Split (Split flow rate: 80 ml/min)

Injected volume: 1.2 µl

Expression of the Results:

The content of the various constituents is expressed in g per 100 g of crude product and is given by the following equation:

$$\% \text{ constituent } i = \frac{Si}{Se} \times \frac{Pe}{P} \times \frac{100}{Ki}$$

With:

Si=surface area of the peak(s) of constituent i

Se=surface area of the internal standard peak

Pe=Weight of internal standard introduced into the beaker (in mg)

P=Weight of sample weighed out (in mg)

Ki=response coefficient of the constituent i

If the percentage obtained (expressed herein on a crude basis) exceeds 20% for one of the constituents, the sample is diluted and the GC analysis recommenced in order to obtain a mass amount of less than 20%.

The mass amounts expressed on a crude basis are then expressed on a dry basis, by dividing for the dry matter content of the sample tested.

The mass amounts of D-allulose, of D-fructose and glucose are easily determined, since none of the characteristic peaks are co-eluted.

The peak of the maltose and of the D-allulose dimers may be co-eluted. However, it should be noted that, in the syrups of the invention and described in the examples below, maltose is never present.

If the characteristic peaks of maltose are not detected, the surface area Si of the D-allulose dimers is determined by integration of the unknown peaks, between 10 and 17 minutes. If the characteristic peaks of maltose are detected (which may be the case in the syrups of the invention), the amounts of maltose are determined and this amount is subtracted from the total amount of the dimers.

In order to determine the total amount of glucose-glucose dimers, the following protocol is carried out on a sample:

Hydrochloric hydrolysis

In a 15 ml hydrolysis tube with a screw cap made of Teflon, weigh out about precisely from 50 to 500 mg of sample (adjust the weighing out according to the expected sugar content), add 2 ml, with a two graduation mark pipette, of the internal standard solution (galactitol at 5 mg/ml in osmosed water), add 3 ml of water and 5 ml of the 4N HCl solution.

Stopper hermetically, stir for 1 min with a vortex stirrer. Place the tube in a thermostatted dry bath regulated at 100° C. for 1 hour, stirring with the vortex from time to time.

Demineralization and concentration

After cooling, deposit the entire hydrolysis in a 50 ml beaker. Add 6 to 8 g of a 50/50 mixture of AG4 X 4 and AG50 W 8 of anionic resin. Leave to stir magnetically for 5 minutes. Filter on paper. Recover the liquor and repeat the demineralization step until a pH close to water is obtained.

Preparation of the sample

In a dish for taring, weigh out 100 to 300 mg of the sample to be tested+10 ml of internal standard solution consisting of methyl α-D-glucopyranoside at 0.3 mg/ml in pyridine. Remove 0.5 ml from the dish for taring and place in a 2 ml pot and evaporate to dryness under a nitrogen stream. Add 20 mg of methoxylamine hydrochloride and 1 ml of pyridine. Stopper and leave in a Reacti-Therm® at 70° C. for 40 min. Add 0.5 ml of BSTFA. Heat for 30 min at 70° C.

The amount of total glucose of the solution (which comprises the initial glucose termed "free" and the glucose resulting from the hydrolysis and in particular linked to the presence of maltose and isomaltose) is determined by GC analysis of the glucose. The amount of maltose and, by the difference between the total amount of dimers attributed to the peaks between 10 and 17 minutes, the amount of D-allulose dimers are easily deduced therefrom.

Example 1: Implementation of a Continuous Industrial Process for Producing D-Allulose Syrup Example 1 consists of a method for continuous production of non-crystallizable D-allulose syrup. The steps of the process used are described in detail in FIG. 1. The composition and the flow rate of the Streams of steps 1 to 5 are described in Table 1a.

Step 1:

17.3 metric tons of a Fructamyl D-fructose syrup (Tereos) comprising 95% of D-fructose at 50% dry matter content (DM) (Stream 1) are introduced into a stirred batch reactor with a working volume of 14 m³. Stream 1 is maintained at 55° C. A lyophilisate of the *Bacillus subtilis* host strain of the D-psicose 3 epimerase enzyme detailed in patent WO 2015/032761 is introduced into the tank in sufficient amount to have $3.3 \times 10^7$ units of activity in the reactor. Three reactors are used sequentially so as to provide a syrup composed essentially of fructose and allulose (Stream 2) continuously at a flow rate of 360 kg/h.

The reaction conditions are the following:

Temperature: 55° C.

pH=7

Reaction time 48 h

At the end of the reaction, the Stream 2 obtained comprises a richness in D-allulose approximately equal to 25% and a richness in D-fructose approximately equal to 75%.

Step 2:

Stream 2 passes through a microfiltration membrane during a batchwise operation. A Stream 3 free of cell debris is obtained, along with a microfiltration retentate (Stream 8) comprising the debris resulting from the *Bacillus subtilis* lyophilisate, which is flushed from the circuit. The microfiltration parameters are as follows:

Transmembrane pressure: 0-3 bar

Pore size: 0.1 µm

Temperature: 50° C.

Mean flow rate: 15 L/h/m²

Membrane: Sepro PS35

Volume Concentration Factor: 33

Step 3:

Stream 3 is demineralized on a Dowex 88 strong cationic resin followed by a Dowex 66 weak anionic resin at a mean flow rate of 2 BV/h. The carboys are maintained at a temperature of 45° C. and the resistivity of Stream 4 at the end of the demineralization remains greater than 100 kΩ·cm⁻¹ at the outlet (Stream 4). When this is not the case, the resins are regenerated.

Step 4:

Stream 4 feeds the continuous chromatography (SCC ARI® equipped with eight columns) of the circuit. The mean feed flow rate is 348 kg/h at 50% DM.

The chromatography parameters are defined as follows:

Volume/column: 2 m$^3$

Resin: Dowex Monosphere 99Ca/320

Temperature: 60° C.

Flow rate water/Stream 4 (vol./vol.): 2.4

Load: 0.09 h$^{-1}$

Two fractions are extracted: the raffinate (Stream 10), and the fraction rich in D-allulose (Stream 5) which goes to step 5. Stream 10 is flushed.

Step 5:

Stream 5 is passed batchwise through a nanofiltration membrane. The parameters are as follows:

Transmembrane pressure: 30 bar

Temperature: 20° C.

Membrane: GE Duracon NF1 8040C35

Volume Concentration Factor VCF: 10

Figure 6:
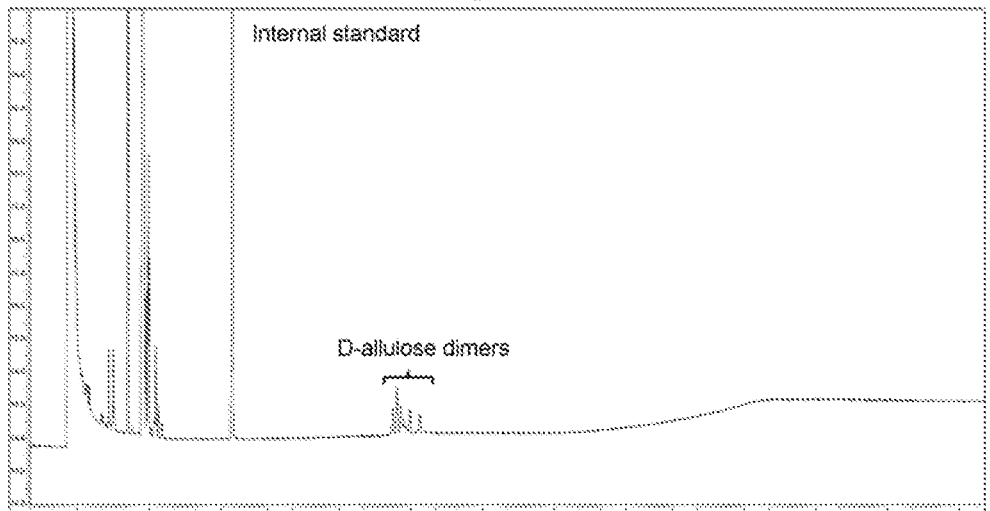
FIG. 6.
Figure 7:
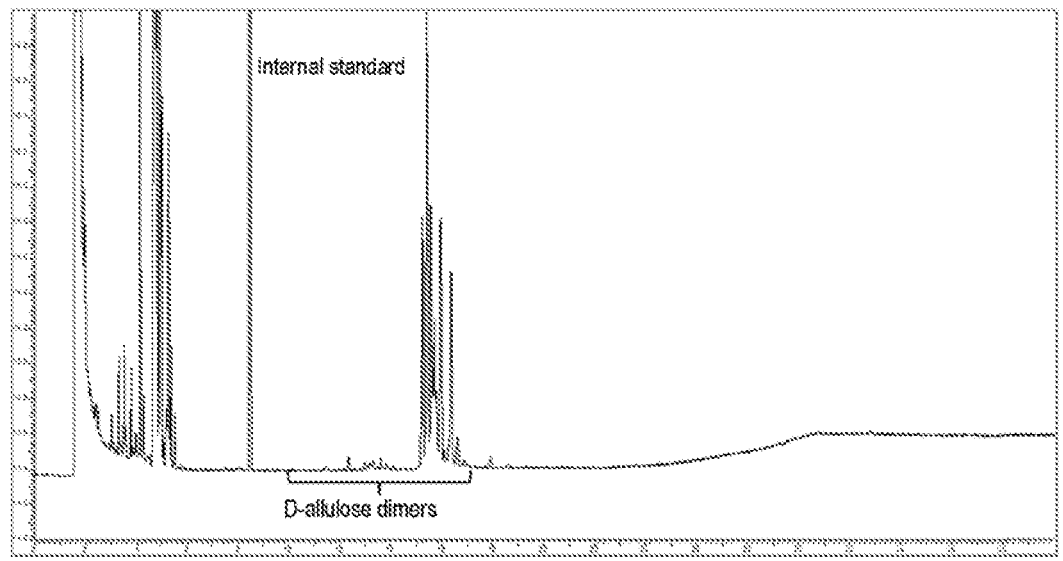
FIG. 7.

The allulose dimers concentrate in the retentate (Stream 6). The permeate (Stream 9) is flushed. FIG. 6 gives the details of the permeation of the syrups as a function of the VCF.

Step 6:

Stream 6 passes through an evaporator. The second stage reaches 77% of dry matter. The D-allulose syrup (Stream 7) is obtained at the end of this step.

The characteristics of the syrup of the invention (Stream 7) are reproduced in Table 1b.

TABLE 1a

Flow rates and composition of the Streams of steps 1 to 5 of Example 1

| Step/Characteristics of | Stream | | |
|---|---|---|---|
| Step 1 | Stream 1 | Stream 2 | — |
| Flow rate by mass (kg/h) | 360 | 360 | |
| Dry matter (%) | 50 | 50 | |
| Fructose Richness (%) | 94.5 | 71.5 | |
| Glucose Richness (%) | 2 | 2 | |
| Allulose Richness (%) | 1 | 24 | |
| Di-Allulose Richness (%) | 1 | 1 | |
| Other Richness (%) | 1.5 | 1.5 | |
| Step 2/Step 3 | Stream 2 | Stream 3 | Stream |
| Flow rate by mass (kg/h) | 360 | 348 | 12 |
| Dry matter (%) | 50 | 50 | 50 |
| Step 4 | Stream 4 | Stream | Stream |
| Flow rate by mass (kg/h) | 348 | 656 | 429 |
| Dry matter (%) | 50 | 20 | 10 |
| Fructose Richness (%) | 71.5 | 93.7 | 3.6 |
| Glucose Richness (%) | 2 | 2.5 | 0.4 |
| Allulose Richness (%) | 23.7 | 0.9 | 93.4 |
| Di-Allulose Richness (%) | 1.2 | 1.1 | 1.5 |
| Other Richness (%) | 1.5 | 1.6 | 1.1 |
| Step 5 | Stream 6 | Stream 9 | — |
| Flow rate by mass (kg/h) | 67.1 | 363.3 | |
| Dry matter (%) | 29.3 | 6.4 | |
| Fructose Richness (%) | 3.5 | 3.7 | |

TABLE 1a-continued

Flow rates and composition of the Streams of steps 1 to 5 of Example 1

| Glucose Richness (%) | 0.4 | 0.4 |
|---|---|---|
| Allulose Richness (%) | 91.8 | 94.8 |
| Di-Allulose Richness (%) | 3.1 | 0.1 |
| Other Richness (%) | 1.2 | 1 |

TABLE 1b

Flow rates and composition of Stream 7

| Step 6 | Stream | — | — |
|---|---|---|---|
| Flow rate by mass (kg/h) | 25.5 | | |
| Dry matter (%) | 77 | | |
| Fructose Richness (%) | 3.5 | | |
| Glucose Richness (%) | 0.4 | | |
| Allulose Richness (%) | 91.8 | | |
| Di-Allulose Richness (%) | 3.4 | | |
| Other Richness (%) | 1.2 | | |

The syrup obtained is non-crystallizable at ambient temperature.

In one and the same process wherein no nanofiltration step is carried out, the D-allulose syrup obtained is similar, with the difference that the amount of D-allulose dimers, expressed by dry mass, is 1.5%.

Example 2: Evaluation of the Crystallizable Nature of the Various D-Allulose Syrups Example 2 consists in preparing various D-allulose syrups having a dry matter content of 77% and a richness in D-allulose of 95% approximately.

These syrups are prepared by adjusting the volume concentration factor of nanofiltration step 5 so as to obtain various Di-allulose contents or by preparing syrups, by mixing the permeate or the retentate obtained with D-allulose crystals or D-fructose crystals and/or by using nanofiltration membranes having a smaller rejection threshold. This made it possible to adjust the contents of the various constituents while keeping the D-allulose content at around 95%. The composition of the dry matter of the syrups appears in Table 2.

In order to evaluate the crystallizable nature of the syrups, a sieved D-allulose Crystal initiator having a mean particle size of 70 μm is introduced into each of the syrups in a proportion of 0.3% (mass of initiator/mass of dry matter).

Each syrup thus initiated is then placed for 4 weeks in a refrigerated chamber at 4° C. or at 15° C.

At the end of this period, the dry matter of the supernatant (or mother liquors) of the sample is measured using the Karl Fischer method. The more the syrup has crystallized, the lower the dry matter of the supernatant (since the dry matter of the syrup has become concentrated in D-allulose crystals).

The initiating carried out during this test makes it possible to carry out, in an accelerated manner, a study of storage stability, in particular at low temperature.

TABLE 2

Composition of the various syrups and dry matter of the supernatant after storage

| | Composition (% GC) | | | | | % DM of the supernatant after one month | |
|---|---|---|---|---|---|---|---|
| | | D-allulose | | | | | |
| Sample | D-allulose | dimer | Glucose | Fructose | Others | 15° C. | 4° C. |
| 1 | 95.1 | 0.1 | 1 | 3.5 | 0.3 | 70.6 | 67.5 |
| 2 | 95 | 0.5 | 0.3 | 3.5 | 0.7 | 71.8 | 68.7 |
| 3 | 94.9 | 0.7 | 0.1 | 3.2 | 1.1 | 72.8 | 69.7 |
| 4 | 95 | 1.2 | 0.2 | 1.9 | 1.7 | 73.4 | 70.2 |
| 5 | 95 | 1.5 | 0.2 | 2 | 1.3 | 73.9 | 70.8 |
| 6 | 95.2 | 2.1 | 0.2 | 1.8 | 0.7 | 74.7 | 71.3 |
| 7 | 95 | 2.7 | 0.2 | 1.4 | 0.7 | 75.3 | 71.6 |
| 8 | 95 | 3 | 0.2 | 4.1 | 0.7 | 75.3 | 71.5 |
| 9 | 95.1 | 3.4 | 0.1 | 1 | 0.4 | 75.6 | 71.6 |
| 10 | 94.9 | 4 | 0 | 1 | 0.1 | 75.3 | 71.5 |
| 11 | 94.8 | 4.6 | 0 | 0.5 | 0.1 | 75.7 | 71.8 |
| 12 | 94.9 | 5 | 0 | 0.1 | 0 | 75.2 | 71.9 |

Figure 8:
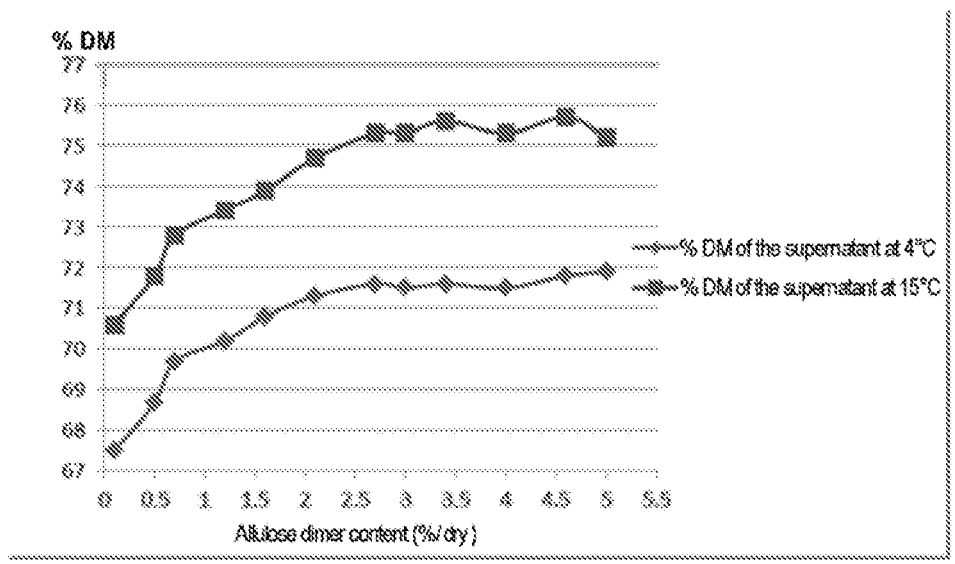
FIG. 8.

These results are represented in FIG. 8.

These tests demonstrate that the dimers of D-allulose are entirely particular compounds, which have a considerable influence on the crystallizable nature of a D-allulose syrup comprising it, contrary for example to glucose or fructose.

Thus, the higher the amount of D-allulose dimer in the syrup, the less crystallizable the D-allulose syrup is, even though the amount of D-allulose remains similar.

These tests demonstrate that the syrups comprising more than 1.5% of D-allulose dimers exhibit a highly improved storage stability at low temperature. This is an advantage since the syrups can thus be more easily handled before use, without having to reheat the syrup (or by reheating it to a lesser extent) so as to at least partly remelt it.

Example 3. Production of Caramels with a Short Texture

A caramel composition with a short (soft) texture comprising the D-allulose syrup according to the invention (Sample 10) was produced.

Table 3 shows the composition of the caramel formulated.

TABLE 3

Caramel formulations using the D-allulose syrup
Amount of ingredients (%) in the formulation

| Ingredients | Formulation |
|---|---|
| Full cream | 27.00 |
| Powdered milk | 8.00 |
| Allulose syrup | 24.40 |
| NUTRIOSE ® FM06 | 23.10 |
| Butter | 5.60 |
| Salt | 0.10 |
| Water | 10.55 |
| Lecithin | 0.20 |
| Sodium bicarbonate | 0.05 |
| Vanilla (2x) | 1.00 |
| Total | 100.00 |
| Nutritional data [a] for 30 g of product | |
| Calories (kcal) | 100.90 |
| Total carbohydrates (g) | 18.80 |
| Sugars (g) | 8.94 |
| Fibers (g) | 8.13 |

TABLE 3-continued

Caramel formulations using the D-allulose syrup
Amount of ingredients (%) in the formulation

| | Formulation |
|---|---|
| Proteins (g) | 0.50 |
| Total fats (g) | 6.69 |

[a] Nutritional data calculated from the product specifications or on the basis of data from the USDA's National Nutrient Database for Standard Reference Release 27, when these specifications were not available The soft caramel obtained from the syrups of the invention has an excellent, very short texture.

Example 4. Production of Ketchup Sauce

A ketchup sauce comprising the D-allulose syrup according to the invention (Sample 10) was produced, along with a reference ketchup sauce.

TABLE 4

Ketchup sauce formulations

| Ingredients | Reference | Invention |
|---|---|---|
| Tomato puree | 35.12 | 35.12 |
| Sucrose | 14.15 | 0 |
| D-Allulose syrup | 0 | 18.54 |
| Modified starch (CLEARAM CH 2020) | 2.44 | 2.44 |
| Vinegar | 13.66 | 13.66 |
| Salt | 0.49 | 0.49 |
| Onion powder | 0.49 | 0.49 |
| Water | 33.66 | 29.47 |
| Total | 100.00 | 100.00 |

The amount of sugars by dry weight of the 2 sauces is equal, but the amount of calories is reduced by 43% with the sauce of the invention. The sauce of the invention has a less sweet taste and is shinier, which is an advantage for a sauce of this type.

The ketchup produced from the syrup of the invention has a smooth texture without aggregates, which is synonymous with non-crystallization of the D-allulose.

Moreover, the ketchup produced from the syrup of the invention exhibits excellent flow, which is due to the fact that the sauce does not crystallize, even after storage for one week in a refrigerator.

Example 5. Production of Barbecue Sauce

A barbecue sauce comprising the D-allulose syrup according to the invention (Sample 10) was produced, along with a reference barbecue sauce.

TABLE 5

| Barbecue sauce formulations | | |
|---|---|---|
| Ingredients | Reference | Invention |
| Tomato sauce | 45.64 | 45.64 |
| D-Allulose syrup | 18.76 | 0.00 |
| Glucose-fructose syrup HFCS 55 (77% DM) | 0.00 | 18.76 |
| Vinegar | 18.26 | 18.26 |
| Modified starch (PREGEFLO CH 20) | 2.28 | 2.28 |
| Liquid smoke | 1.62 | 1.62 |
| Salt | 1.50 | 1.50 |
| Garlic powder | 0.63 | 0.63 |
| Onion powder | 0.53 | 0.53 |
| Mustard powder | 0.30 | 0.30 |
| Paprika | 0.20 | 0.20 |
| Dye | 0.13 | 0.13 |
| Water | 10.14 | 10.14 |
| Total | 100.00 | 100.00 |

Method

The ingredients in dry form are weighed out and mixed together. The tomato sauce and the water are mixed in a mixer and then the ingredients in dry form are added. After integration of these ingredients in dry form, the syrup and the vinegar are added and mixed well. The mixture is placed in a dish and heated until the water content is approximately 74%.

Characteristics

| | Reference | Invention |
|---|---|---|
| Dry matter | 26.5% | 27.3% |
| Taste | Sweet | Slightly less sweet than the reference sauce |
| Viscosity, texture | Smooth and sufficiently viscous to be "dippable" | Smooth and sufficiently viscous to be "dippable" |

Nutritional Information for 35 g of Product

| | Reference | Invention |
|---|---|---|
| Calories (kcal) | 26.7 | 11.4 |
| Carbohydrates (g) | 6.31 | 6.31 |
| Sugars (g) | 5.17 | 5.17 |
| Fibers (g) | 0.83 | 0.83 |
| Proteins (g) | 0.34 | 0.34 |
| Fats (g) | 0.29 | 0.29 |

The sauce of the invention has a calorie content reduced by 57% while at the same time comprising the same amount of sugars.

Although it is viscous, the sauce of the invention has a very smooth texture, which is synonymous with non-crystallization of the D-allulose.

Example 6. Production of Jam

A jam comprising the D-allulose syrup according to the invention (Sample 10) was produced, along with a reference jam.

TABLE 6

| Jam formulations | | |
|---|---|---|
| Ingredients | Reference | Invention |
| Strawberries | 49.27 | 49.27 |
| D-Allulose syrup | 0.00 | 49.27 |
| Glucose-fructose syrup HFCS 55 (77% DM) | 49.27 | 0.00 |
| Modified pectin | 0.45 | 0.45 |
| Citric acid (50% solution) | 1.01 | 1.01 |
| Total | 100.00 | 100.00 |

The strawberries are washed and crushed and the seeds are removed. The strawberry puree, the syrup and the pectin are mixed and heated in a heat-proof dish. After a few minutes of boiling, the heat-proof dish is removed from the heat so as to obtain a dry matter of approximately 57%, the citric acid is added and the mixture is left to cool.

Organoleptic Characteristics

| | Reference | Invention |
|---|---|---|
| Dry matter | 57.4% | 57.2% |
| Taste | Sweet | Slightly less sweet and more acidic than the reference |
| Viscosity, texture in the mouth | Smooth and spreadable | Smooth and spreadable |

Nutritional Information for 17 g of Jam

| | Reference | Invention |
|---|---|---|
| Calories (kcal) | 34.2 | 8.8 |
| Carbohydrates (g) | 8.62 | 8.59 |
| Sugars (g) | 8.28 | 8.31 |

Observations:

The jam prepared from D-allulose syrup does not darken during cooking. This is expected due to the fact that the pH is acidic and that it does not comprise unmodified protein. The calorie content of the jam of the invention has the advantage of having a calorie content reduced by 74%. The color of the jam of the invention is slightly more colored (more red) than the reference jam, which is an advantage for a jam.

The jam produced from the syrup of the invention also has the advantage of having a smooth texture, similar to the reference jam using a very slightly crystallizable syrup (it comprises a mixture of glucose and fructose in virtually equivalent amounts).

Example 7. Use of the Syrup as an Adhesive Agent of a Deep-Frozen Pizza Topping In this example, the D-allulose syrup according to the invention (Sample 10) was used.

Generally, the cheese of the topping of deep-frozen pizzas has a tendency to detach from the pizza. A layer of adhesive agent, which can be a glucose-fructose syrup, is thus used in order to improve the adhesion. However, excessively fast crystallization of the adhesive agent can cause the cheese to separate from the pizza, rather than making it adhere. The adhesive agent would have an advantage in being less sweet.

Protocol

A pizza dough is rolled out and then placed in an oven at 245° C. for 8 minutes.

After baking, the dough is cooled and then covered with pizza sauce. Next, the pizza is optionally sprayed with 4 g of syrup (or of water), 50 g of grated mozzarella is sprinkled on and then the pizza is optionally re-sprayed with 4 g of syrup (or of water).

The pizza covered with aluminum foil is placed in a freezer for 4 days. The aluminum foil is then removed from said pizza. A first test consists in turning over the frozen pizza: the cheese which falls from the pizza is recovered. A second test consists in doing likewise, with the pizza being turned over when it is thawed.

The pizza is then baked and a sensory analysis is carried out.

TABLE 7

Results obtained

| Adhesive agent | Concentration | Amount (g) of cheese lost (frozen) | Amount (g) of cheese lost (thawed) | Sensory analysis |
|---|---|---|---|---|
| HFCS 42 | 50% solution | 0 | 0 | Too sweet |
| D-allulose syrup purity 95%, 75% DM | 50% solution | 0 | 0 | Slightly sweet |
| D-allulose syrup purity 95%, 75% DM | 10% solution | 0 | 0 | Taste not modified compared with the reference |
| Control | — | 8 | 16 | Reference |
| Tap water | tap water | 5 | 14 | Taste not modified compared with the reference |

No loss of cheese was observed for the pizza (thawed or not) using the adhesive agent obtained from the syrup of the invention, just like the HFCS 42 agent, but which itself has a sweeter taste than the reference pizza. The reference pizza, for its part, loses 32% of cheese when it is thawed and then turned over. According to the same test, if water is used as adhesive agent, 28% of the cheese is lost.

Example 8. Ice Cream Composition

The reduced-sugar ice cream composition was prepared according to the following recipe:

| | |
|---|---|
| Powdered skimmed milk | 400 g |
| Water | 1801.2 g |
| Stabilizer | 12 g |
| Sucrose | 160 g |
| Allulose | 440 g |
| Vanilla | 28 g |
| Full cream | 1160 g |
| Total | 4000 g |

The ice cream obtained has a texture which is creamy and smooth in the mouth.

The invention claimed is:

1. D-allulose syrup comprising, in addition to the D-allulose, a mass content of D-allulose dimer, determined by gas chromatography (GC), greater than 1.5%.

2. D-allulose syrup according to claim 1, wherein the D-allulose dimer content ranges from 1.9% to 20%.

3. D-allulose syrup according to either of the preceding claim 1, wherein it has a D-allulose content greater than or equal to 75%.

4. D-allulose syrup according to claim 1, wherein it comprises, relative to its dry mass:
   from 75% to 99% of D-allulose;
   from 0% to 20% of D-fructose;
   from 0% to 10% of glucose;
   from 1.5% (limit excluded) to 20% of D-allulose dimer.

5. D-allulose syrup according to claim 1, wherein it has a dry matter content greater than 50%.

6. Process for producing a D-allulose syrup according to claim 1, wherein it comprises:
   a step of providing a D-allulose composition comprising D-allulose dimers;
   a step of nanofiltration of said D-allulose composition;
   a step of recovering the nanofiltration retentate;
   a step of concentrating this retentate so as to provide the D-allulose syrup.

7. Process according to claim 6, wherein a step of chromatography of a composition comprising D-allulose and D-fructose is carried out so as to provide the D-allulose composition.

8. Process according to claim 7, wherein the composition comprising D-allulose and D-fructose is obtained by epimerization of a D-fructose solution.

9. D-allulose syrup that can be obtained by means of the process of claim 6.

* * * * *